United States Patent
Shuman

(10) Patent No.: US 10,610,206 B2
(45) Date of Patent: Apr. 7, 2020

(54) VACUUM ASSISTED SAMPLING MECHANISM

(71) Applicant: Spiration Inc., Redmond, WA (US)

(72) Inventor: Brandon J. Shuman, Kirkland, WA (US)

(73) Assignee: Spiration, Inc., Redmond, WA (US)

( * ) Notice: Subject to any disclaimer, the term of this patent is extended or adjusted under 35 U.S.C. 154(b) by 139 days.

(21) Appl. No.: 15/673,028

(22) Filed: Aug. 9, 2017

(65) Prior Publication Data

US 2019/0046166 A1    Feb. 14, 2019

(51) Int. Cl.
*A61B 10/00*    (2006.01)
*A61B 10/02*    (2006.01)
*A61B 10/04*    (2006.01)

(52) U.S. Cl.
CPC .. *A61B 10/0283* (2013.01); *A61B 2010/0208* (2013.01); *A61B 2010/045* (2013.01)

(58) Field of Classification Search
CPC ............. A61M 1/3643; A61M 1/3646; A61M 2202/0464; A61M 1/3647; A61M 1/0023; A61M 5/14216; A61M 27/006; A61B 10/02; A61B 10/0283; A61B 2010/0208; A61B 2010/045; A61B 10/0045
See application file for complete search history.

(56) References Cited

U.S. PATENT DOCUMENTS

| | | | | |
|---|---|---|---|---|
| 4,051,852 A * | 10/1977 | Villari | ............. | A61M 39/02 604/183 |
| 4,447,235 A * | 5/1984 | Clarke | ............. | A61B 17/3415 600/573 |
| 5,002,528 A * | 3/1991 | Palestrant | ............. | A61M 3/0241 604/246 |
| 5,334,315 A * | 8/1994 | Matkovich | ............. | A61M 1/3643 210/136 |
| 5,496,281 A * | 3/1996 | Krebs | ............. | A61B 17/3401 604/168.01 |
| 6,217,556 B1 * | 4/2001 | Ellingson | ............. | A61B 10/0283 604/167.01 |
| 2016/0354595 A1 * | 12/2016 | Gallagher | ............. | A61B 10/0283 |
| 2017/0055966 A1 * | 3/2017 | Vetter | ............. | A61B 10/0266 |

* cited by examiner

*Primary Examiner* — Eric J Messersmith

(57) ABSTRACT

An exemplary pumping-syringe device for allowing an operator to control a vacuum in a medical device and to expel samples without disconnecting the pumping-syringe device from the medical device. The pumping-syringe device includes a syringe section, a valve section that sealably connects to the syringe and a fitting section connected to the syringe section and the valve section and detachably connects to the medical device. The valve section includes two modes of operation. A first mode of operation allows fluid flow in a first direction between the syringe section and an external environment and a second mode of operation allows fluid flow in a second direction between the syringe section and the external environment.

5 Claims, 4 Drawing Sheets

VACUUM ASSISTED SAMPLING MECHANISM

BACKGROUND

Currently sample devices, for example transbronchial needle aspiration (TBNA), include a stylet that is used to assist in sample collection. After puncture with the needle, the stylet inside the needle is pulled back which may help draw tissue into the needle due to creation of reduced pressure.

Other sampling techniques include applying a back and forth technique with the needle to "pack" the tissue into the needle tip.

These methods apply very little vacuum to the tissue and thus, are not reliable tissue extraction techniques.

Another technique uses a vacuum syringe. After puncture, a vacuum is drawn in a syringe and applied to the inside of the needle. This helps draw the tissue up inside. But once the syringe has fully retracted, no more vacuum action can occur. For example, if there is lots of fluid, it will be pulled in first reducing the vacuum to be applied to the (non-fluid) tissue.

Also, tissue may get stuck inside the needle after aspiration. A stylet can be used to push out the tissue or the operator can inject some air using an air source. However, the stylet may damage the sample and attaching air source would make it a more difficult procedure requiring more personnel to successfully complete.

SUMMARY

The present invention provides a pumping-syringe device that allows the operator to control an applied vacuum and to expel samples without disconnecting the devices used and connect other supporting devices.

An exemplary pumping-syringe device includes a syringe section, a valve section configured to sealably connect to the syringe and a fitting section connected to the syringe section and the valve section and configured to detachably connect to a medical device (e.g., needle handle). The valve section can operate in two different modes. A first mode of operation allows fluid flow in a first direction between the syringe section and an external environment, but not in a second direction. A second mode of operation allows fluid flow in the second direction between the syringe section and the external environment, but not in the first direction.

In one aspect of the invention, the first direction begins at the external environment and proceeds to the syringe section and the second direction begins at the syringe section and proceeds to the external environment.

In another aspect of the invention, the valve section includes a first junction having three ports, a first one-way valve, a second one-way valve, a 3-way valve and a connector tube. A first port of the first junction sealably connects to the first port of the syringe section. A second port of the first junction sealably connects to a first end of the connector tube. A third port of the first junction sealably connects to a first end of the first one-way valve. A second end of the first one-way valve sealably connects to a first port of the 3-way valve. A second end of the connector tube sealably connects to a first end of the second one-way valve. A second end of the second one-way valve sealably connects to a second port of the 3-way valve.

In still another aspect of the invention, the syringe section includes a plunger located within a chamber. A distal side of the plunger within the chamber is in fluid communication with the fitting section and at least a portion of the valve section.

In a yet another aspect of the invention, the fitting section includes a mechanism for detachably connected to the medical device. The medical device includes a needle device and the mechanism includes a Luer lock component.

Instead of back and forth on the needle, the operator can leave the needle in place, and pump the tissue inside. Each pump of the device will increase the vacuum or simple apply more vacuum pressure. So faster and more cycles on the pump brings more tissue into the needle. The operator controls how much ore little vacuum to generate by the number of pumps or speed of pumping.

Similarly, this device can be used in reverse and used to pump the sample out of the tip of the needle. The operator has the ability to draw the sample in and eject the sample incrementally, methodically and slowly rather than rely only on the vacuum in the syringe, as with the current methods.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings:

FIG. 1-2 shows a prior art medical device that is connectable to the pumping-syringe device of FIG. 1-1;

FIG. 2 shows the device of FIG. 1-1 connected to the medical device of FIG. 1-2;

DETAILED DESCRIPTION

Figure 1:
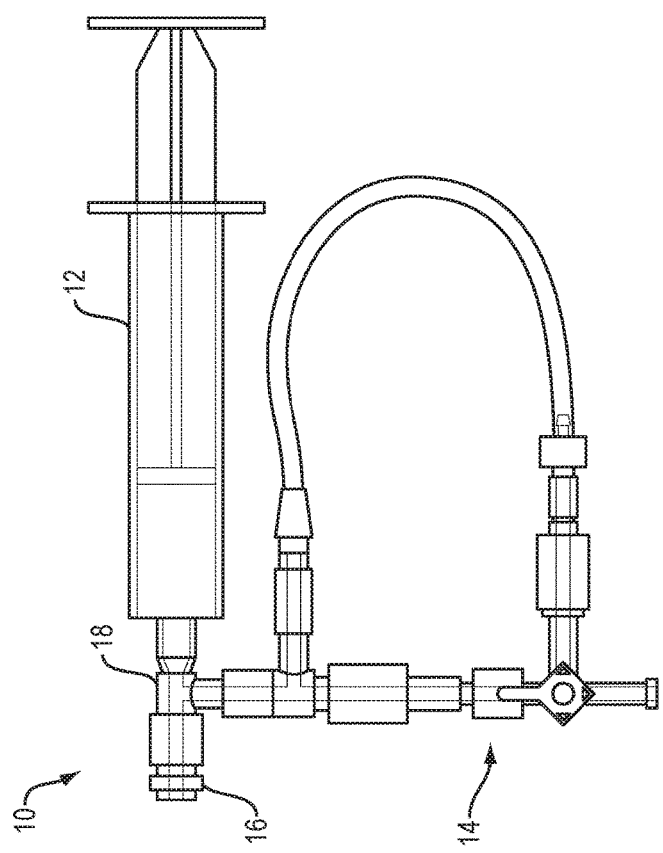
FIG. 1-1 shows a side view of a pumping-syringe device formed in accordance with an embodiment of the present invention.

In one embodiment, as shown in FIG. 1-1, a pumping-syringe system 10 includes a syringe 12, a valve section 14 and a connector 16, all of which are connected to a junction fitting 18. The syringe 12 and the connector 16 are connected to the junction fitting 18 such that they share a longitudinal axis. The valve section 14 connects to the junction fitting 18 at some angle from the longitudinal axis of the syringe 12 and the connector 16. The one or more of the components may be formed of a monolithic material. Other axis sharing (alignment) configurations may be used between the components.

Figures 1, 2:
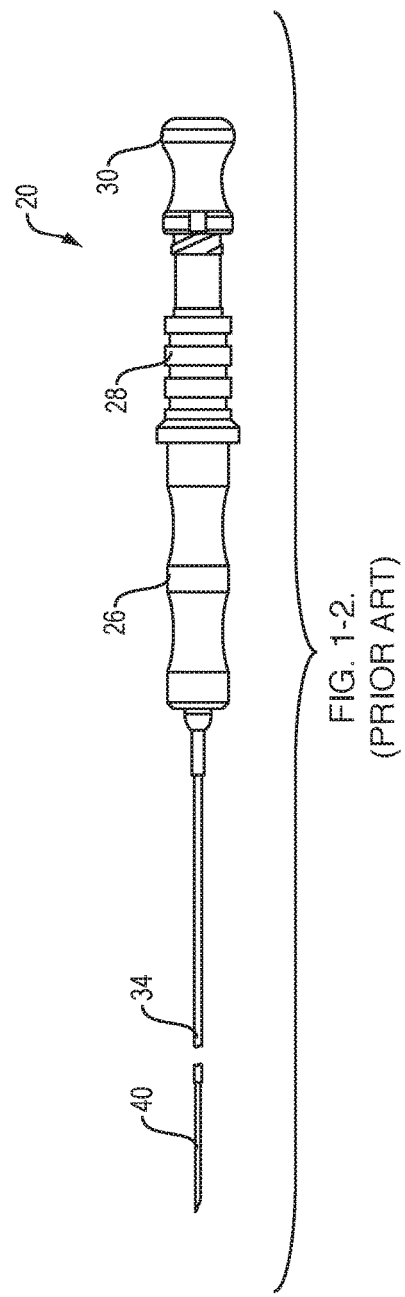
Figure 2:
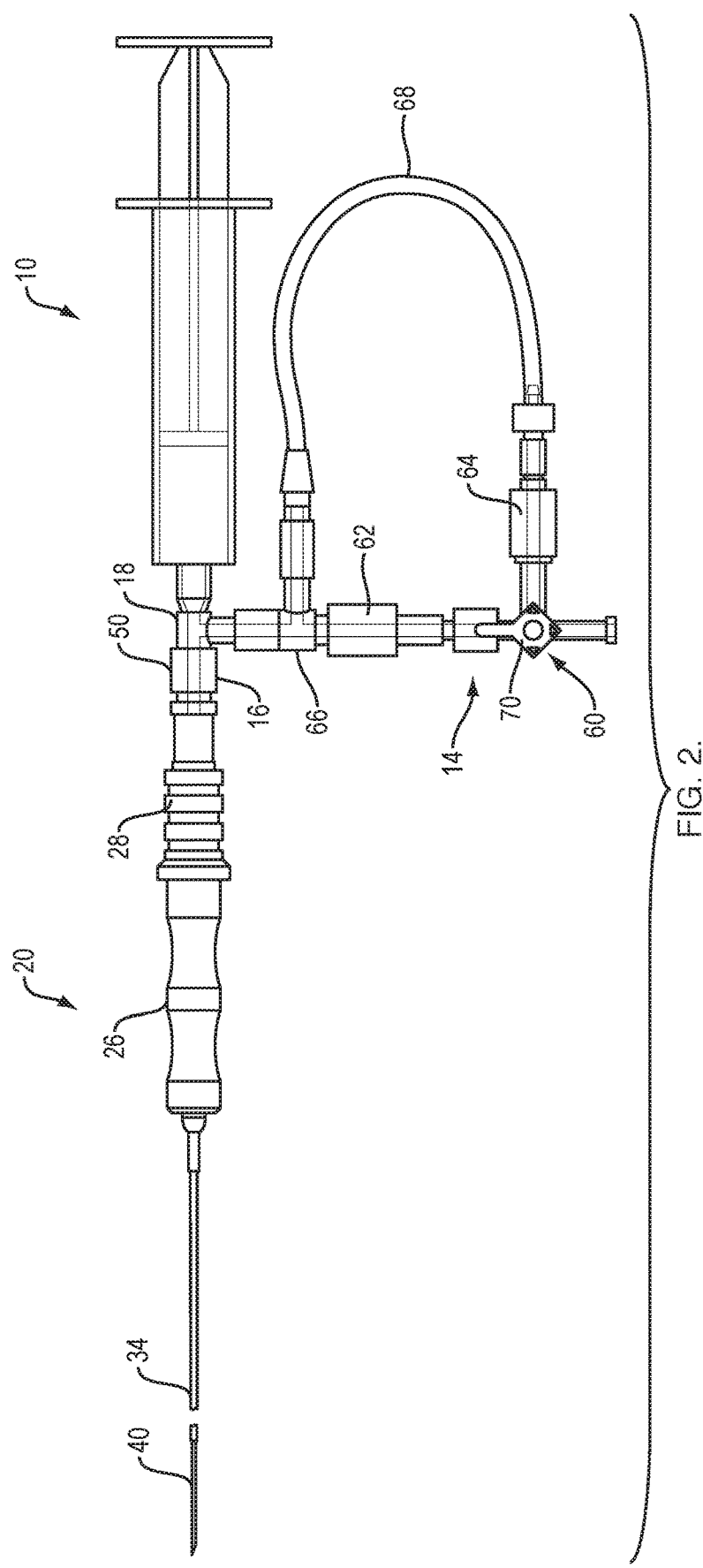

The pumping-syringe system 10, via the connector 16, is connectable to any number of medical devices, such as a needle handle 20 (FIG. 1-2) or a scope (e.g., bronchoscope). In one embodiment, as shown in FIG. 2, the connector 16 includes an inner cavity that includes a threaded feature 50 (e.g., Luer fitting) for attaching to a proximal end of the needle handle 20.

The valve section 14 includes a 3-way valve 60, a first one-way valve 62, a second one-way valve 64, a tee fitting 66 and a flexible connector tube 68. The tee fitting 66 includes a major longitudinal axis that is shared by a first port and a second port and a minor longitudinal axis for a third port. The first port sealably attaches to the junction fitting 18. A first end of the flexible connector tube 68 sealably attaches to the third port. A first end of the first one-way valve 62 sealably attaches to the second port.

A second end of the first one-way valve 62 is sealably connected to a first port of the 3-way valve 60. A first end of the second one-way valve 64 is sealably connected to a second end of the flexible connector tube 68. A second end of the second one-way valve 64 is sealably connected to a second port of the 3-way valve 60. A third port of the 3-way valve 60 is free of connections with direct access to surrounding environment. Other axial configuration connections may be applied between the components.

The 3-way valve 60 includes a valve knob 70 that can be placed in at least two positions. A first position causes the third port of the 3-way valve 60 to be in fluidic communication with the first port of the 3-way valve 60. A second position causes the third port of the 3-way valve 60 to be in fluidic communication with the second port of the 3-way valve 60.

Figure 3:
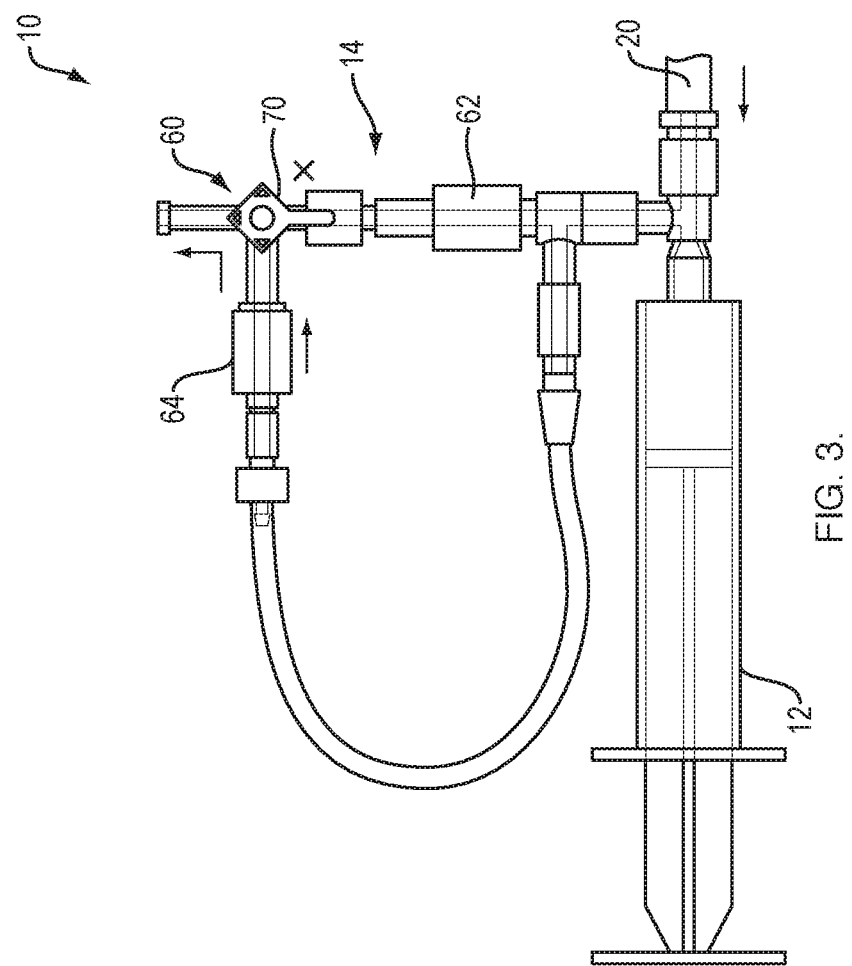
FIG. 3 shows the device of FIG. 1-1 in a first mode of operation.

In a suction mode of operation of the pumping-syringe system 10, as shown in FIG. 3, the valve knob 70 is placed in the second position before an operator commences with retraction of the plunger of the syringe 12. The second and third ports of the 3-way valve 60 are in fluidic connection. The second one-way valve 64 only allows air or fluid to pass towards the 3-way valve 60 while blocking air or fluid between the 3-way valve 60 and the flexible connector tube 68. In this configuration, the syringe 12 connected to the needle device 20 causes a vacuum to occur at the distal end of the needle device 20 while the operator of the syringe 12 pulls the syringe plunger in a proximal direction (i.e., to the left in FIG. 3). In order to perform the pumping action, the operator forces the plunger in a distal direction after having retracted the plunger, thus causing expulsion of air through the junction fitting 18, the tee fitting 66, the flexible connector tube 68, the second one-way valve 64, then into the 3-way valve 60 and out the third port of the 3-way valve 60. The process described above can be repeated, thus allowing for repeatable application of the vacuum at the distal end of the attached device.

Figure 4:
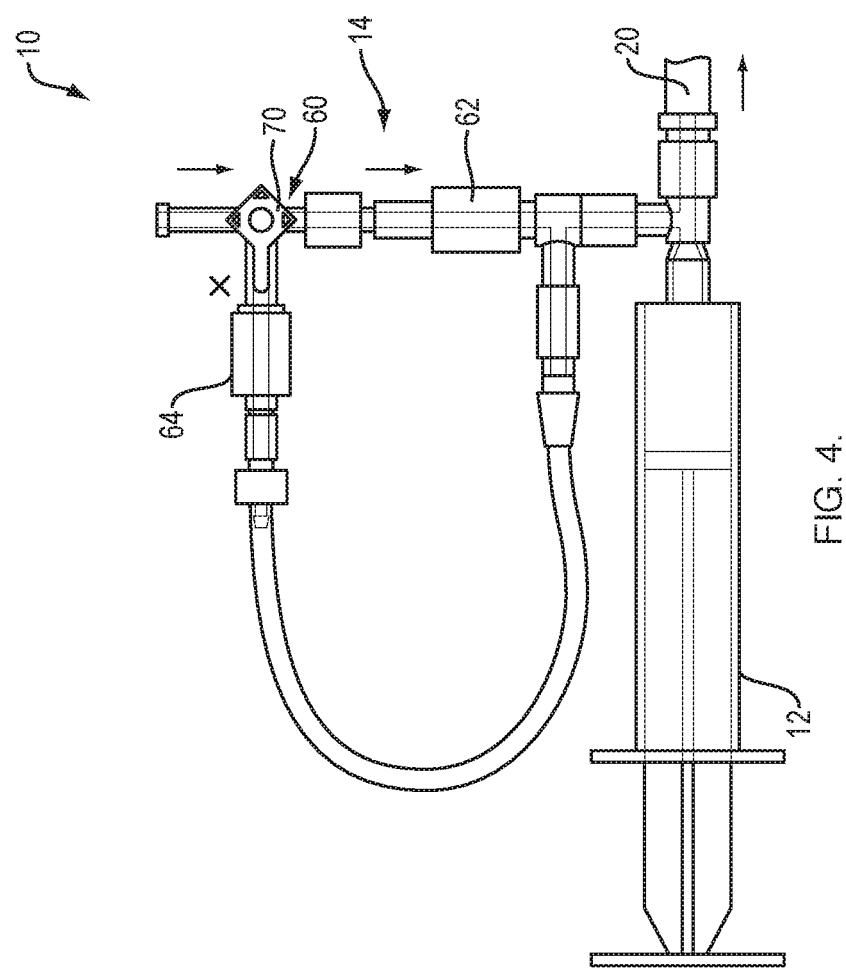
FIG. 4 shows the device of FIG. 1-1 in a second mode of operation.

In a second mode of operation of the pumping-syringe system 10, as shown in FIG. 4, the valve knob 70 is placed in the first position before an operator commences with expulsion (i.e., distal movement of the plunger of the syringe 12). The first and third ports of the 3-way valve 60 are in fluidic connection. The first one-way valve 62 only allows air or fluid to pass from the 3-way valve 60 to the junction fitting 18. This allows the operator to pull air into the chamber of the syringe 12 from the valve section 14 without pulling a vacuum at the distal end of the needle device 20. When the operator forces the plunger in the distal direction (to the right in FIG. 4), the air in the chamber of the syringe 12 is forced through the junction fitting 18 and into the needle device 20. This produces an air pressure force at the distal end of the needle device 20 causing expulsion of any tissue or other materials previously received within the distal end of the needle 40.

In one embodiment, the valve section 14 may be replaced by a reversible or 2-way check valve (not shown). The reversible or 2-way check valve would include a switch for controlling the functional direction of the valve.

A. A pumping-syringe device comprising: a syringe section; a valve section; and a fitting section connected to the syringe section and the valve section and configured to detachably connect to a medical device, wherein the valve section includes two modes of operation, a first mode of operation allows fluid flow in a first direction between the syringe section and an external environment and a second mode of operation allows fluid flow in a second direction between the syringe section and the external environment.

B. The device of B, wherein the first direction is from the external environment to the syringe section and the second direction is from the syringe section to the external environment.

C. The device of B, wherein the first mode of operation does not allow fluid flow in the second direction and the second mode of operation does not allow fluid flow in the first direction.

D. The device of C, wherein the valve section comprises: a first junction comprising three ports; a first one-way valve; a second one-way valve; a 3-way valve; and a connector tube.

E. The device of D, wherein a first port of the first junction sealably connects to a port of the fitting section, a second port of the first junction sealably connects to a first end of the connector tube, a third port of the first junction sealably connects to a first end of the first one-way valve, a second end of the first one-way valve sealably connects to a first port of the 3-way valve, a second end of the connector tube sealably connects to a first end of the second one-way valve, a second end of the second one-way valve sealably connects to a second port of the 3-way valve.

F. The device of A, wherein the syringe section comprises a plunger located within a chamber, wherein a distal side of the plunger within the chamber is in fluid communication with the fitting section and at least a portion of the valve section.

G. The device of A, wherein the fitting section comprises a mechanism for detachably connecting to the medical device.

H. The device of G, wherein the medical device comprises a needle with a handle, wherein the mechanism comprises a Luer lock component on a proximal end of the handle.

The description of the invention is merely exemplary in nature and variations that do not depart from the gist of the invention are intended to be within the scope of the invention. Such variations are not to be regarded as a departure from the spirit and scope of the invention.

Although the preferable embodiments of the present invention have been described hitherto, the present invention is not limited to these embodiments. Additions, omissions, substitutions, and other modifications can be made without departing from the spirit or scope of the present invention.

In addition, the invention is not limited by the above description and is limited by only the scope of appended claims.

What is claimed is:
1. A pumping-syringe device comprising:
a syringe section;
a valve section comprising:
 a first junction comprising three ports;
 a first one-way valve;
 a second one-way valve;
 a 3-way valve; and
 a connector tube; and
a fitting section connected between the syringe section and the valve section and configured to detachably connect directly to a medical device, wherein the valve section includes two modes of operation, a first mode of operation allows fluid flow in a first direction between the syringe section and an external environment and a second mode of operation allows fluid flow in a second direction between the syringe section and the external environment, wherein the first direction is from the external environment to the syringe section and the second direction is from the syringe section to the external environment, wherein the first mode of operation does not allow fluid flow in the second direction and the second mode of operation does not allow fluid flow in the first direction.

2. The device of claim 1, wherein a first port of the first junction sealably connects to a port of the fitting section, a second port of the first junction sealably connects to a first end of the connector tube, a third port of the first junction sealably connects to a first end of the first one-way valve, a second end of the first one-way valve sealably connects to a first port of the 3-way valve, a second end of the connector tube sealably connects to a first end of the second one-way valve, a second end of the second one-way valve sealably connects to a second port of the 3-way valve.

3. The device of claim 1, wherein the syringe section comprises a plunger located within a chamber, wherein a distal side of the plunger within the chamber is in fluid communication with the fitting section and at least a portion of the valve section.

4. The device of claim 1, wherein the fitting section comprises a mechanism for detachably connecting to the medical device.

5. The device of claim 4, wherein the medical device comprises a needle with a handle, wherein the mechanism comprises a Luer lock component on a proximal end of the handle.

* * * * *